United States Patent [19]

Das

[11] Patent Number: 4,638,011
[45] Date of Patent: Jan. 20, 1987

[54] TETRAHYDROTHIENYL SUBSTITUTED PROSTAGLANDIN ANALOGS

[75] Inventor: Jagabandhu Das, Plainsboro, N.J.

[73] Assignee: E. R. Squibb & Sons, Inc., Princeton, N.J.

[21] Appl. No.: 682,713

[22] Filed: Dec. 17, 1984

[51] Int. Cl.$^4$ .................... A61K 31/38; C07D 333/24
[52] U.S. Cl. ...................................... 514/438; 549/79
[58] Field of Search .......................... 549/79; 514/438

[56] References Cited

U.S. PATENT DOCUMENTS

| | | |
|---|---|---|
| 4,143,054 | 3/1979 | Sprague . |
| 4,187,236 | 2/1980 | Sprague . |
| 4,220,594 | 9/1980 | Sprague . |
| 4,228,180 | 10/1980 | Sprague . |
| 4,254,044 | 3/1981 | Sprague . |
| 4,542,151 | 9/1985 | Das ........................................ 549/79 |

FOREIGN PATENT DOCUMENTS 0043292 8/1982 European Pat. Off. .
2039909 8/1980 United Kingdom .

Primary Examiner—Alan Siegel
Attorney, Agent, or Firm—Lawrence S. Levinson; Burton Rodney

[57] ABSTRACT

Tetrahydrothienyl substituted prostaglandin analogs are provided having the structural formula

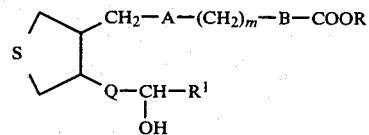

and including all stereoisomers thereof.

The compounds are cardiovascular agents useful, for example, in the treatment of thrombolytic disease.

18 Claims, No Drawings

TETRAHYDROTHIENYL SUBSTITUTED PROSTAGLANDIN ANALOGS

DESCRIPTION OF THE INVENTION

The present invention relates to tetrahydrothienyl substituted prostaglandin analogs which are cardiovascular agents useful, for example, in the treatment of thrombolytic disease. These compounds have the general formula

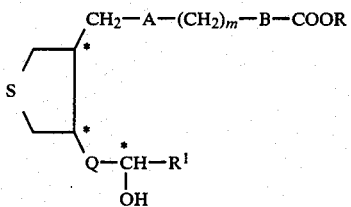

and including all stereoisomers thereof, wherein A is —(CH$_2$)$_2$—, —CH=CH— or a single bond; m is 1 to 8 is a single bond or —CH=CH— but where B is —CH=CH—, m is 1 to 6; R is H, lower alkyl or alkali metal; Q is —CH=CH— or —(CH$_2$)$_2$—; and R$^1$ is lower alkyl, aryl, aralkyl, cycloalkyl, cycloalkylalkyl or lower alkoxy.

The term "lower alkyl" or "alkyl" as employed herein by itself or as part of another group includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or CF$_3$, an alkoxy substituent, an aryl substituent (for example,

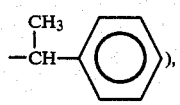

an alkyl-aryl substituent, a haloaryl substituent, a cycloalkyl substituent or an alkylcycloalkyl substituent.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be lower alkyl, halogen (Cl, Br or F), or lower alkoxy.

The term "aralkyl", "aryl-alkyl" or "aryl-lower alkyl" as used herein by itself or as part of another group refers to lower alkyl groups as discussed above having an aryl substituent, such as benzyl or methylbenzyl

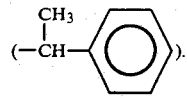

The term "cycloalkylalkyl" as used herein by itself or as part of another group refers to cycloalkyl groups as defined above linked to an alkyl group as defined above.

The term "lower alkoxy", "alkoxy" or "aralkoxy" by itself or as part of another group includes any of the above lower alkyl, alkyl or aralkyl groups linked to an oxygen atom.

The terms "halogen" or "halo" as used herein by itself or as part of another group refers to chlorine, bromine, fluorine or iodine with chlorine being preferred.

The terms "(CH$_2$)$_m$" and "(CH$_2$)$_2$" includes straight or branched chain radicals having from 1 to 8 carbons in the normal chain in the case of (CH$_2$)$_m$ and 2 carbons in the normal chain in the case of (CH$_2$)$_2$, and may contain one or more lower alkyl substituents. Examples of (CH$_2$)$_m$ and (CH$_2$)$_2$ groups include CH$_2$,

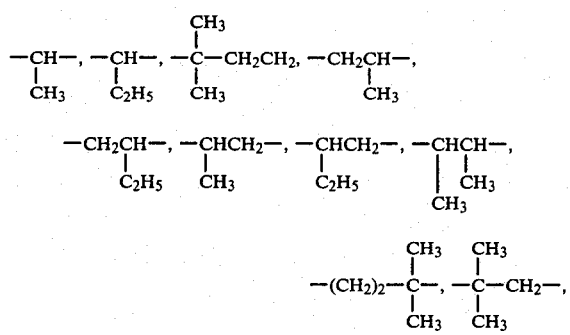

(CH$_2$)$_3$, (CH$_2$)$_4$, (CH$_2$)$_5$, (CH$_2$)$_6$, (CH$_2$)$_7$,

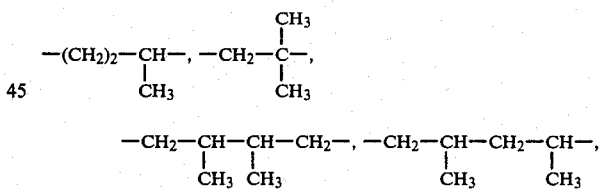

and the like.

Preferred are those compounds of formula I wherein A is —CH=CH— or —(CH$_2$)$_2$—, B is a single bond, m is 2 or 5, Q is —CH=CH—, R is hydrogen and R$^1$ is lower alkyl, phenyl, cycloalkyl or benzyl.

The various compounds of the invention may be prepared as outlined below.

The compounds of formula I of the invention are prepared from the aldehyde intermediate II

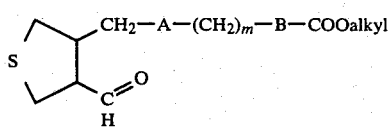

the preparation of which is described below.

The aldehyde intermediate II

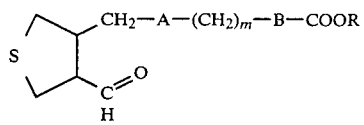   II wherein A is —CH=CH may be prepared as follows.

1-Trimethylsilyloxy-1,3-butadiene A is an inert organic solvent such as methylene chloride, ether or tetrahydrofuran is made to react with maleic anhydride B in a Diels-Alder reaction to form the anhydride C

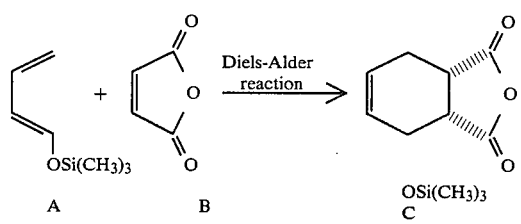

The anhydride C is treated with concentrated hydrochloric acid in the presence of an inert organic solvent such as tetrahydrofuran to form the desilylated adduct D

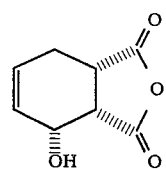

which is then reacted with dihydropyran in the presence of dry methylene chloride and p-toluenesulfonic acid to form the tetrahydropyranyl ether E

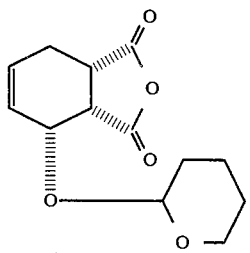

The tetrahydropyranylether E is reduced, for example, by treatment with a reducing agent such as lithium aluminum hydride, in the presence of an inert organic solvent such as tetrahydrofuran to form diol F

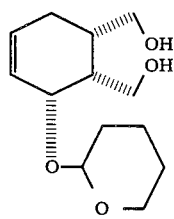

The diol F is then reacted with dimethylaminopyridine and methyl chloroformate in the presence of an inert organic solvent such as methylene chloride and a base such as pyridine to form bis-methylcarbonate G

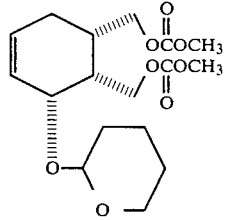

which is then made to undergo osmylation by reacting G with osmium tetroxide in the presence of N-methylmorpholine-N-oxide and appropriate inert organic solvent such as tetrahydrofuran to form diol H

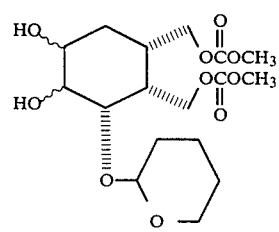

The diol H is next subjected to periodate cleavage by reacting it in an alcohol solvent such as methanol with sodium metaperiodate to form dialdehyde J

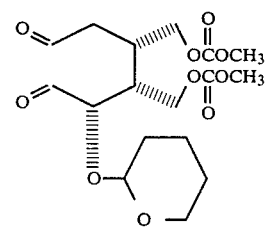

The dialdehyde J is then reduced by treatment with sodium borohydride in the presence of an inert organic solvent such as methanol or tetrahydrofuran, to form the diol K

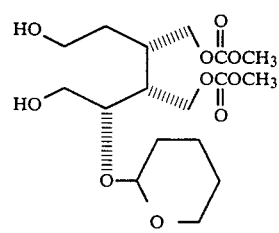

which is then subjected to acetonide formation by treating K with dry Amberlyst-15 acid resin in the presence of methanol and acetone to form the alcohol L

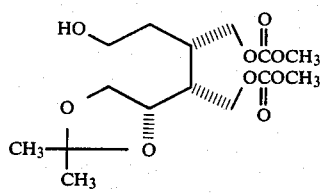
L which is treated with p-toluene sulfonic acid and dihydropyran in the presence of an inert organic solvent such as methylene choride, to form tetrahydropyranyl ether M

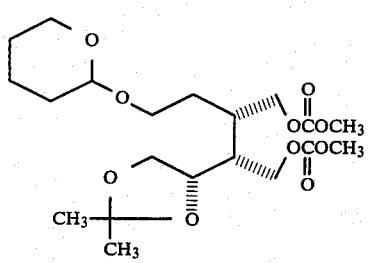
M which is then reduced to the diol N by treating M with lithium aluminum hydride in the presence of an inert solvent such as tetrahydrofuran

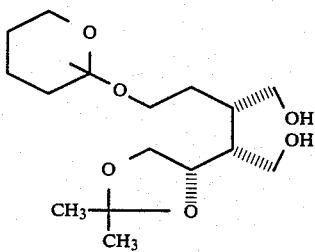
N

The diol N is then reacted with methanesulfonyl chloride in the presence of an organic solvent such as pyridine to form the bis-mesylate O

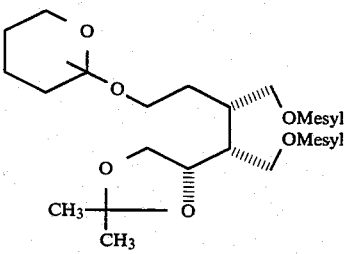
O

The bis-mesylate O in dimethylsulfoxide or methanol is treated with sodium sulfide nonahydrate in dimethyl sulfoxide or ethanol to form the tetrahydrothiophane P

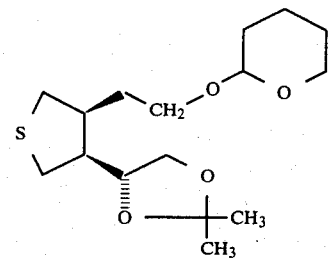
P which is treated with Amberlyst-15 resin in the presence of methanol and acetone to form the alcohol Q

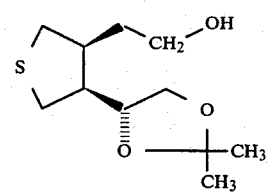
Q

Alcohol Q is then treated with dimethylsulfoxide in the presence of oxalyl chloride and methylene chloride and then with triethylamine to form the aldehyde R

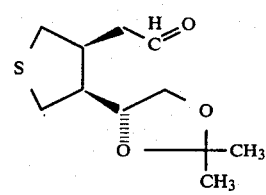
R

Aldehyde R is next subjected to a Wittig reaction wherein a mixture of triphenylphosphonium compound S

$(C_6H_5)_3P\text{-}A\text{-}(CH_2)_m\text{-}B\text{-}COOH \cdot Br$ such as (4-carboxybutyl)-triphenylphosphonium bromide salt in tetrahydrofuran and potassium t-amylate in toluene is reacted with aldehyde R to form acid T

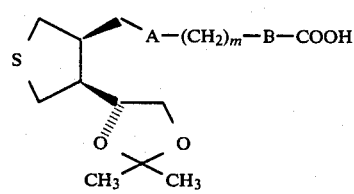
T which is then dissolved in ether and reacted with diazomethane to form ester U

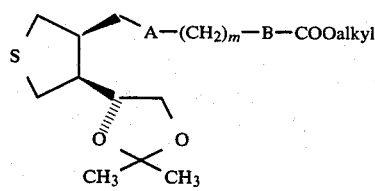
U

Ester R is then made to undergo acetal exchange by reacting R in methanol with p-toluene sulfonic acid to form diol V

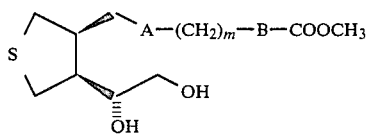  V which is then subjected to periodate cleavage by reacting V in methanol with sodium metaperiodate to form aldehyde IIA

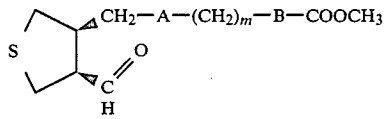  IIA

The intermediate aldehyde of formula II wherein A is —$(CH_2)_2$— are prepared by reducing compound V by treatment with hydrogen in the presence of palladium on charcoal to form compound V'

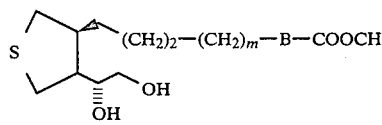  V' which is subjected to periodate cleavage as described above to form aldehyde IIAA

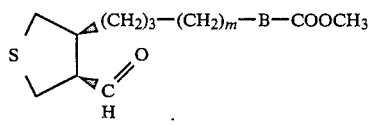  IIAA

The aldehyde II, IIA or IIAA may be employed as an intermediate in forming the cis series of compounds, that is

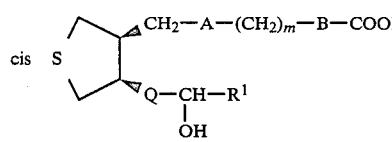  IA as opposed to the trans series whose preparation is described later

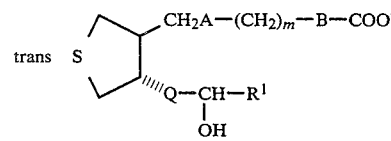  IB

In forming the cis series of the invention wherein Q is CH=CH, the aldehyde II, IIA or IIAA is subjected to a phosphonate reaction wherein the aldehyde is reacted with a phosphonate W.

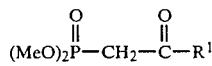  W in the presence of sodium hydride and dimethoxyethane or in the presence of lithium bromide and triethylamine in an inert organic solvent such as methylene chloride or acetonitrile to form enone III

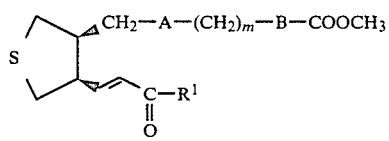  III which is reduced by treating III with a reducing agent such as sodium borohydride or zinc borohydride in the presence of cerium trichloride and methanol to form allylic alcohols IV and IVA

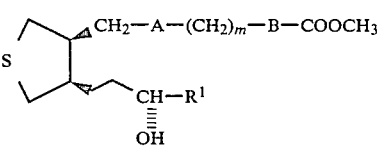  IV

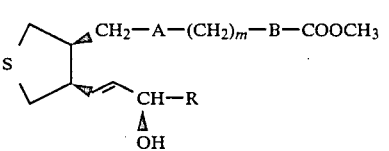  IVA

Allylic alcohol compounds IV and IVA may be separated on a silica gel column and the desired allylic alcohol may then be hydrolyzed by treatment with a strong base such as lithium hydroxide, potassium carbonate or sodium hydroxide to form the corresponding alkali metal salt which is treated with strong acid such as HCl to form the acid of the invention V or VA

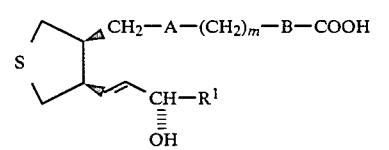  V

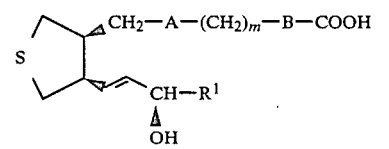  VA

The aldehyde II, IIA or IIAA may be employed as an intermediate in forming the trans series IB as follows. The aldehyde II, IIA or IIAA is subjected to an epimerization reaction wherein the aldehyde in methanol is reacted with sodium methoxide to form the aldehyde VI

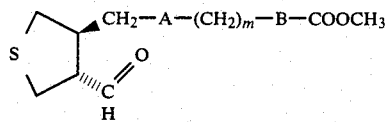

which is subjected to a phosphonate reaction as described above wherein VI is reacted with phosphonate W

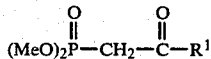

in the presence of sodium hydride and dimethoxyethane to form enone VII

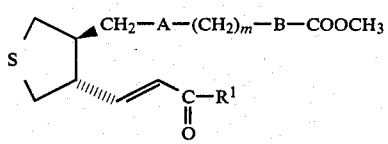

which is reduced by treating VII with a reducing agent such as sodium borohydride or zinc borohydride in the presence of cerium trichloride and methanol to form allylic alcohols VIII and VIIIA

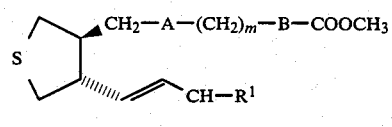

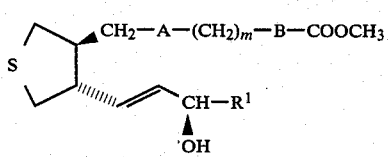

Allylic alcohols VIII and VIIIA may be separated on a silica gel column and the desired allylic alcohol may then be hydrolyzed by treatment with a strong base such as lithium hydroxide, potassium carbonate or sodium hydroxide to form the corresponding alkali metal salt which is treated with strong acid such as HCl to form the acid of the invention IX or IXA

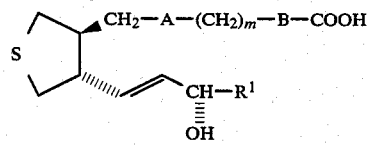

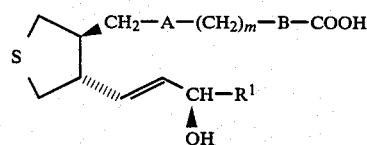

Compounds of formula I of the invention wherein B is —CH=CH— and m is 1 to 6 may be prepared by subjecting any of the alcohols of the invention of the structure

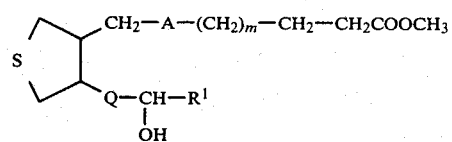

wherein
Q is CH=CH or $(CH_2)_2$,
A is CH=CH, a single bond or $(CH_2)_2$, to tetrahydropyranyl ether formation by reacting alcohol X with dihydropyran in the presence of an inert organic solvent such as methylene chloride, chloroform and catalytic amounts of p-toluene sulfonic acid at reduced temperatures of from about 0° C. to about 10° C., to form the tetrahydropyranyl ether of formula XI

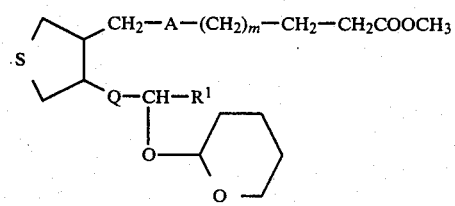

The tetrahydropyranyl ether XI is then subjected to phenylselenylation by reacting XI with lithium diisopropyamlde at reduced temperatures of from about −78° C. to less than about 0° C. in the presence of an inert organic solvent such as tetrahydrofuran, dimethoxy ethane or ether; thereafter a solution of diphenyldiselenide in an inert organic solvent as described above is added and the reaction is mainted at reduced temperatures as descirbed above to form the selenophenyl ester XII

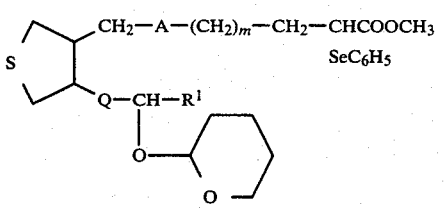

The selenophenyl ester XII is hydrolyzed by treatment with a base such as lithium hydroxide, potassium carbonate or sodium hydroxide in the presence of an inert organic solvent such as tetrahydrofuran, methanol or dimethoxyethane-water and then with a strong acid such as HCl to form the acid XIII

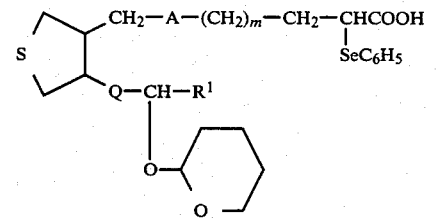

Acid XIII is then oxidized by reaction with hydrogen peroxide in the presence of an inert organic solvent such as tetrahydrofuran at reduced temperatures of from about 0° C. to about 25° C. to form the α,β-unsaturated acid XIV

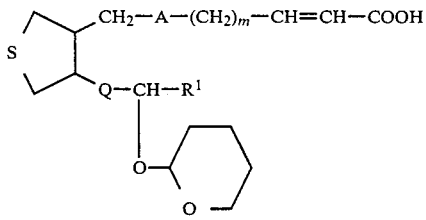

which is then hydrolyzed by treatement with strong acid such as HCl in the presence of an inert organic solvent such as dimethoxyethane-water to form XV

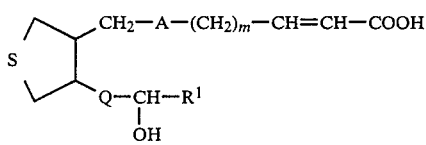

Compounds of formula I wherein Q is —(CH$_2$)$_2$— may be prepared by subjecting any of the intermediates of the invention of the structure XVI

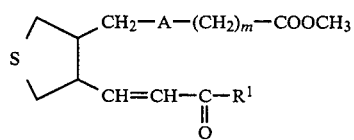

to a reduction procedure wherein XVI is treated with a mixture of cuprous bromide and sodium bis(2-methoxyethoxy) aluminum hydride at a reduced temperature of from about −78° C. to about 0° C. to form XVII

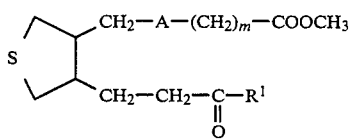

which is then treated with cerium trichloride and sodium borohydride as described above with respect to conversion of III→IV and VII→VIII, to form

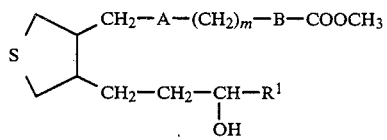

which may then be hydrolyzed to the corresponding acid XIX

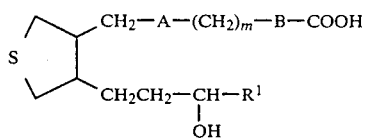

Compounds of formula I wherein Q is —(CH$_2$)$_2$— may also be prepared by reducing any of the intermediates

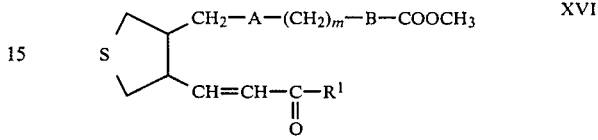

by treatment with sodium borohydride in the presence of pyridine to form alcohol XVIII which may then be hydrolyzed to the corresponding acid XIX by treatment with alkali metal hydroxide and then HCl as described hereinbefore.

The compounds of this invention have three centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, all cis and all trans forms and stereoisomeric pairs may be prepared as shown in the working Examples which follow.

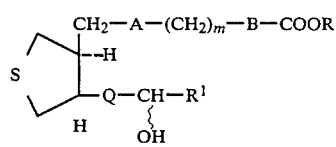

cis

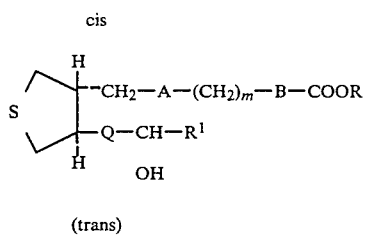

(trans)

The wavy ( ) line in the above formulae indicates that the hydroxy group in each of the compounds of formulae IA-ID is either R(β) or S(α).

The compounds of this invention are cardiovascular agents useful in inhibiting arachidonicinduced platelet aggregation, e.g., for treatment of thrombolytic disease, such as coronary or cerebral thromboses, and in inhibiting bronchoconstriction as associated with asthma. They are also selective thromboxane A$_2$ receptor antagonists and synthetase inhibitors, e.g., having a vasodilatory effect for treatment of myocardial ischemic disease, such as angina pectoris. They can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The compounds of this invention may also be administered topically to treat peripheral vascular diseases and as such may be formulated as a cream or ointment.

The compounds of this invention when used in combination with a cyclic AMP phosphodiesterase inhibitor such as theophylline or papaverine may be used in the preparation and to prolong storage of platelet concentrates.

The following Examples represent preferred embodiments of the invention. Unless otherwise indicated, all temperatures are expressed in degrees Centigrade.

EXAMPLE 1

[3α(Z),4α(1E,3S)]-7-[Tetrahydro-4-(3-hydroxy-1-octenyl)-3-thienyl]-5-heptenoic acid, methyl ester

A. (1α,2β,3β)-1-Trimethylsiloxycyclohex-5-ene 2,3-dicarboxylic acid anhydride To a solution of 23.6 ml of 1-trimethylsilyloxybutadiene (133.33 mmol) in 200 ml of dry methylene chloride was added with stirring 10 g of maleic anhydride (100 mmole). The homogeneous reaction mixture was stirred at room temperature for 24 hours, whereupon most of the methylene chloride was removed by distillation under reduced pressure. The crude oil was presoaked in silica gel and loaded on a 200 g silica gel column. Elution with 10–25% ethyl acetate in hexane and finally with 50% ethyl acetate in hexane gave 23.13 g of desired title adduct as a colorless oil.

B. (1α,2β,3β)-1-Hydroxycyclohex-5-ene-2,3-dicarboxylic acid anhydride

To a solution of 10 g of Part A tri-methylsilyloxy adduct (41.7 mmole) in 50 ml of distilled THF was added with stirring 1 ml of concentrated hydrochloric acid. The reaction mixture was stirred at room temperature for 2 hours, whereupon it was filtered through a pad of anhydrous magnesium sulfate. The filtrate was concentrated under reduced pressure to obtain the title desilylated adduct.

C. (1α,2β,3β)-1-Tetrahydropyranyloxycyclohex-5-ene-2,3-dicarboxylic acid anhydride The crude Part B desilylated adduct was dissolved in 50 ml of dry methylene chloride and cooled in an ice-water bath. To this solution was added 5.6 ml of reagent grade dihydropyran, followed by 30 mg of p-toluene sulfonic acid. After stirring for 1 hour at 0°–5° C., the reaction mixture was washed with saturated sodium bicarbonate solution. The aqueous layer was extracted with ether. The combined organic extract was dried over anhydrous magnesium sulfate and concentrated under reduced pressure. The crude residue was chromatographed on a silica gel column and eluted with 10–20% ethyl acetate in hexane to obtain 9.33 g of desired title tetrahydropyranyl ether as a colorless oil (93% yield).

D. (1α,2β,3β)-1-Tetrahydropyranyloxycyclohex-5-ene-2,3-dimethanol

To a suspension of 2.28 g of 95% pure lithium aluminum hydride in 300 ml of freshly distilled THF (60 mmole), cooled in an ice-water bath was added dropwise a solution of 9.33 g of Part C anhydride (38.2 mmole) in 50 ml of dry THF over a period of 45 minutes. After the addition was complete, the cooling bath was removed and the reaction mixture was allowed to stand at room temperature overnight, whereupon it was again placed on an ice-water bath and excess of LAH was destroyed by careful addition of freshly prepared saturated sodium sulfate solution. Addition of sodium sulfate was continued until all the lithium and aluminum salts were precipitated as a granular solid. Solid magnesium sulfate was added to the reaction mixture and it was then filtered. The residue was washed several times with methylene chloride. Finally the residue was taken up in 1000 ml of a 10% acetonitrile in ethyl acetate and stirred for 30 minutes. It was then filtered. Combined filtrate was concentrated under reduced pressure to obtain an oily residue. The crude residue was chromatographed on a silica gel column and eluted with 20–50% ethyl acetate in hexane to obtain 8.17 g of desired title diol as a viscous oil (~93% yield).

E. (1α,2β,3β)-1-Tetrahydropyranyloxycyclohex-5-ene-2,3-dimethanol bismethyl carbonate To a solution of 7.767 g of Part D diol (31.83 mmole) in 100 ml of dry methylene chloride and 10 ml of pyridine (250 mmole) cooled at 0° C. was added with stirring 390 mg of 4-dimethylamino pyridine (3.2 mmole, 10 mole %) followed by 5.8 ml of methyl chloroformate (75 mmole, 1.17 equiv) dropwise. An immediate precipitate of pyridinium hydrochloride was observed. The reaction mixture was maintained at 0° C. for additional 4 hours, whereupon it was washed thoroughly with water and then with saturated copper sulfate solution. The aqueous extracts were extracted with ether (X3). The combined organic extract was washed with water, saturated salt solution and finally was dried over magnesium sulfate. Evaporation of solvent under reduced pressure gave an oil which was chromatographed on a 250 g silica gel column and eluted with 5–15% ethyl acetate in hexane to obtain 10.87 g of desired title bis-methylcarbonate (95% yield) which solidified on standing in the cold room.

F. (1α,2β,3β)-1-Tetrahydropyranyloxy-5,6-dihydroxy cyclohexane-2,3-dimethanol-bismethyl carbonate To a solution of 5.13 g of Part E bis-methylcarbonate (14.25 mmole) in 30 ml of distilled THF was added with stirring 2.16 g of crystalline N-methylmorpholine N-oxide (16 mmole). Water was added dropwise to the reaction mixture, until it became homogeneous. To this homogeneous solution was now added 100 ml of a solution of osmium tetroxide (250 mg/5 ml of ether) in ether. The reaction mixture was stirred at room temperature for 30 hours, whereupon aqueous sodium bisulfate solution was added to the reaction mixture. The solution was stirred for additional 30 minutes, whereupon the organic layer was separated and the aqueous layer was extracted several times with methylene chloride. The combined organic extract was washed with saturated salt solution, dried over anhydrous magnesium sulfate and finally was concentrated under reduced pressure. Trituration with ether gave a white precipitate which was filtered off and washed with cold-ether. 3.88 g of crystalline diol were obtained as white solid. The filtrate was concentrated under reduced pressure and the residue was chromatographed on a silica gel column. Elution with 30–50% ethyl acetate in hexane and finally with ethyl acetate gave an additional 987 mg of crystalline title diol. Total yield=4.867 g (~87% yield).

G.
2-[1-Formyl)methyl]-3-[(1-tetrahydropyranyloxy-1-formyl)methyl]butane-1,4-bismethyl carbonate To a solution of 3.67 g of crystalline Part F diol (~10 mmole) in 15 ml of methanol and 15 ml of distilled THF, cooled in an ice-water bath was added with stirring a solution of 1.75 g of powdered sodium-metaperiodate (15 mmole) in 15 ml of water. After the addition was over, the reaction mixture was stirred vigorously at 0°–5° C. for 1 hour and finally at room temperature for an additional 4 hours, whereupon TLC indicated complete disappearance of the diol. The crude reaction mixture was diluted with ether and washed thoroughly with water. The aqueous layer was reextracted with ether (X3). The combined organic extract was dried over anhydrous magnesium sulfate and finally was concentrated under reduced pressure to obtain the crude title dialdehyde as a colorless oil.

H.
2-[(1-Hydroxymethyl)methyl]-3-([1-tetrahydropyranyloxy-1-hydroxymethyl)methyl]butane-1,4-bismethyl carbonate The crude dialdehyde was now dissolved in 25 ml of methanol and cooled at −10° C. in a dry ice-acetone bath and 380 mg of solid sodium borohydride (10 mmole) was added in portions with stirring. After stirring at −10° C. to +5° C. for 1 hour, aqueous ammonium chloride solution was added to the reaction mixture. It was then extracted with ether (X3) and then with methylene chloride (X3). The combined organic extract was dried over anhydrous magnesium sulfate and finally was concentrated under reduced pressure to obtain 3.83 g of crude title diol as a viscous oil.

I.
2-[(2-Hydroxyethyl)]-3-[(3,3-dimethyl-2,4-dioxa)cyclopentyl]butane-1,4-bismethyl carbonate To a solution of 3.83 g of crude Part H diol from the previous reaction in 20 ml of dry methanol and 20 ml of dry acetone (dried over molecular sieves) was added with stirring 800 mg of powdered and dry Amberlyst-15 acid resin. The heterogeneous reaction mixture was stirred under an argon atmosphere overnight, whereupon it was diluted with ether and filtered through anhydrous magnesium sulfate. Residual molecular Amberlyst resin was thoroughly washed with ether. The filtrate was concentrated under reduced pressure and the crude residue was chromatographed on a silica gel column. Elution with 20–50% ethyl acetate in hexane gave 2.85 g of desired title acetonide alcohol (87% overall yield from six membered Part F diol) as a colorless viscous oil.

J.
2-[(2-Tetrahydropyranyloxy)ethyl]-3-[(3,3-dimethyl-2,4-dioxa)cyclopentyl]butane-1,4-bismethyl carbonate To a solution of 2.65 g of Part H acetonidealcohol (7.6 mmole) in 40 ml of dry methylene chloride was added with stirring at 0°–5° C. (ice-water bath) a catalytic amount of p-toluenesulfonic acid and 750 μl of dihydropyran (8.3 mmole). The reaction mixture was stirred under dark at 0°–5° C. for 1 hour, whereupon it was washed with aqueous sodium bicarbonate solution. The aqueous layer was extracted with ether (X2). The combined organic extract was dried over anhydrous magnesium sulfate, filtered and the filtrate was concentrated under reduced pressure. The crude oily residue was chromatographed on a silica-gel column and eluted with 5–10% ethyl acetate in hexane to obtain 3.02 g of desired title tetrahydropyranyl ether which crystallized on standing at −20° C. (92% yield).

K.
2-[(2-Tetrahydropyranyloxy)ethyl]-3-[(3,3-dimethyl-2,4-dioxa)cyclopentyl]butane-1,4-diol To a suspension of 380 mg of lithium aluminum hydride (10 mmole) in 15 ml of freshly distilled THF, cooled in an ice-water bath was added with stirring, dropwise a solution of 2.75 g of Part J bis-carbonate (6.3 mmole) in 10 ml of dry THF over a period of 15 minutes. After the addition was over, the reaction mixture was stirred at 0°–5° C. and finally at room temperature for 3 hours, whereupon it was placed in a cold-bath and an excess of hydride was carefully decomposed by slow addition of saturated sodium sulfate solution. Addition of saturated sodium sulfate solution was continued until all the inorganic salts were precipitated as a white granular solid. Solid magnesium sulfate was added to the reaction mixture and it was then filtered. The residue was thoroughly washed with THF and methylene chloride (1:1). The combined filtrate was concentrated under reduced pressure. The crude oily residue was chromatographed on a silica gel column and eluted with 50% ethyl acetate in hexane followed by ethyl acetate to obtain 1.85 g of desired title diol as a viscous oily residue (92.5% yield).

L.
2-[(2-Tetrahydropyrahyloxy)ethyl]-3-[(3,3-dimethyl-2,4-dioxa)cyclopentyl]butane-1,4-bismesylate To a solution of 960 μl of methanesulfonylchloride (12 mmole) in 10 ml of pyridine, cooled at -10° C. in a dry ice-acetone bath was added with stirring, a solution of 1.61 g of Part K diol (5.07 mmole) in 2 ml of pyridine and 5 ml of methylene chloride, dropwise over a period of 10 minutes. After the addition was over, the reaction mixture was allowed to warm to 0° C. and left at 0°–5° C. for 3 hours, whereupon it was diluted with ether and washed thoroughly with water and saturated copper sulfate solution to remove pyridine. The aqueous wash was extracted with ether (X3). The combined organic extract was washed with water, dried over anhydrous magnesium sulfate and concentrated under reduced pressure. The crude oily title bis-mesylate residue was further dried in vacuo and was then immediately used in the next reaction.

M.
(3α,4β)-2-[Tetrahydro-4-(4,4-dimethyl-3,5-dioxacyclopentyl)-3-thienyl]ethanol, tetrahydropyranyloxy ether 2.4 g of recrystallized sodium sulfate nonahydrate (crystallized from hot ethanol) was added to 70 ml of dry dimethyl sulfoxide. Roughly 25 ml of dimethyl sulfoxide was removed by distillation under reduced pressure (bath temperature 90° C.). The reaction mixture was cooled to room temperature and the distillation head was replaced with a reflux condenser. A solution of the crude Part C bis-mesylate (~5.07 mmole) in 5 ml of dimethyl sulfoxide and 5 ml of ether was added dropwise with stirring over a period of 5 minutes. The reaction mixture was now heated to 70° C. and maintained at that temperature for 3 hours, whereupon it was cooled, diluted with ether and washed thoroughly with water. The aqueous layer was re-extracted with ether (X2). The combined ether extract was dried over anhydrous magnesium sulfate and finally was concentrated under reduced pressure. The crude residue was chromatographed on a silica gel column and eluted with 5–15% ethyl acetate in hexane to obtain 1.36 g of desired title tetrahydrothiophane as an oil. 86% yield in two steps from diol).

N.
(3α,4α)-2-[Tetrahydro-4-(4,4-dimethyl-3,5-dioxacyclopentyl)-3-thienyl]ethanol To a solution of 1.56 g of Part M tetrahydrothiophene-THP ether (4.93 mmole) in 10 ml of dry methanol and 10 ml of dry acetone was added with stirring 450 mg of dried and crushed Amberlyst-15 resin. The reaction mixture was stirred at room temperature under an argon atmosphere for 6 hours, whereupon it was diluted with ether and filtered through anhydrous magnesium sulfate. The filtrate was concentrated under reduced pressure and the crude oily residue was chromatographed on a silica gel column. Elution with 30% ethyl acetate in hexane, followed by 50% ethyl acetate in hexane and finally with ethyl acetate gave 1.06 g of desired title alcohol as a white crystalline solid (92.5% yield).

O.
(3α,4α)-2-[Tetrahydro-4-(4,4-dimethyl-3,5-dioxacyclopentyl)-3-thienyl]-acetaldehyde To a solution of 400 μl of distilled oxalylchloride (5 mmole) in 10 ml of anhydrous methylene chloride, cooled at −78° C. in a dry ice-acetone bath was added with stirring, dropwise 800 μl of dry dimethylsulfoxide (11.2 mmole) over a period of 10 minutes. A rapid gas evolution occurred during its addition. After 20 minutes at −78° C., a solution of 712 mg of Part N alcohol (2.93 mmole) in 5 ml of methylene chloride was added dropwise at −78° C. over a period of 5 minutes. Additional stirring was continued for 30 minutes, whereupon 1.5 ml of distilled triethylamine was added at −78° C. After stirring at −78° C. for 20 minutes, the cooling bath was removed and the reaction mixture was warmed to 0° C., whereupon water was added to the reaction mixture. The reaction mixture was allowed to stand at room temperature for an additional 5 minutes, whereupon it was diluted with ether and washed thoroughly with water. The aqueous layer was extracted with ether (X3). The combined ether extract was dried over anhydrous magnesium sulfate and finally was concentrated under reduced pressure to obtain 727 mg of title aldehyde as an oily residue. This was used in the Wittig reaction without any additional purifications.

P.
[3α(Z),4α]-7-[Tetrahydro-4-(4,4-dimethyl-3,5-dioxacyclopentyl)-3-thienyl]-5-heptenoic acid and

Q.
[3α(Z),4α]-7-[Tetrahydro-4-(4,4-dimethyl-3,5-dioxacyclopentyl)-3-thienyl]-5-heptenoic acid, methyl ester To a suspension of 2.66 g of carboxybutyltriphenylphosphonium bromide (6 mmole) in 20 ml of freshly distilled THF, cooled in an ice-water bath was added with stirring 7.2 ml of 1.4M solution of K-t-amylate in toluene, dropwise. After the addition, the water bath was removed and the orange ylide suspension was stirred at room temperature for an additional 2 hours. It was again cooled in an ice-water bath and a solution of 727 mg of crude title O aldehyde (2.93 mmole) in 5 ml of dry THF was added dropwise. The reaction mixture was stirred at room temperature for an additional 1 hour, whereupon it was quenched by addition of glacial acetic acid. The reaction mixture was now diluted with ether and washed successively with water and saturated sodium bicarbonate solution (X3). The combined aqueous layer was extracted with ether (X2). The combined ether extract was dried over anhydrous magnesium sulfate and finally was concentrated under reduced pressure. The crude residue was triturated with ether and the precipitated phosphine oxide was filtered off. The filtrate was placed in a cold-water bath and etheral diazomethane solution was added with stirring until the yellow diazomethane color persisted for 15 minutes. Excess diazomethane was now removed by bubbling argon through the reaction mixture. It was now concentrated under reduced pressure and the crude residue was chromatographed on a silica gel column. Elution with 10-30% ethyl acetate in hexane gave 683 mg of desired title Q Wittig addition product (70% yield from alcohol) contaminated with ~15% of the undesired E-olefin.

R.
(3α(Z),4α]-7-[Tetrahydro-4-(1,2-dihydroxyethyl)-3-thienyl]-5-heptenoic acid, methyl ester To a solution of 683 mg of Part Q acetonide (1.93 mmole) in 10 ml of anhydrous methanol was added with stirring a catalytic amount of p-toluene sulfonic acid (~5 mg). The reaction mixture was stirred at room temperature under an argon atmosphere for 24 hours, whereupon it was concentrated under reduced pressure and the crude residue was chromatographed on a silic gel column. Elution with 20% ethyl acetate in hexane gave 110 mg of unreacted acetonide. Further elution with 50% ethyl acetate in hexane and finally with ethyl acetate gave 427 mg of desired title diol (84% yield based on a recovered acetonide) as a colorless oil.

S.
[3α(Z),4α]-7-[Tetrahydro-4-formyl-3-thienyl]-5-heptenoic acid, methyl ester To 90 mg of Part R diol (0.31 mmole) in 2 ml of methanol at 25° C. was added a solution of 75 mg of sodium metaperiodate (0.34 mmole, 1.1 equiv.) in 1 ml of $H_2O$. After stirring at 25° C. for 1 hour, the reaction mixture was concentrated. The residue was diluted with 3 ml of H₂O, then extracted with three 10 ml portions of CH₂Cl₂. The combined organic layer was dried over anhydrous MgSO₄ and concentrated to give 80 mg of crude title aldehyde as a yellow oil. This was used immediately in the next reaction.

T.
[3α(Z),4α(1E)]-7-[Tetrahydro-4-(3-oxo-1-octenyl)-3-thienyl-5-heptenoic acid, methyl ester To a slurry of 33.6 mg of prewashed sodium hydride (50% in mineral oil, 0.76 mmole, 2.2 equiv.) in 4 ml of dry dimethoxyethane (DME) was added at 0° C. under an argon atmosphere 206 mg of 2-oxoheptyl dimethyl phosphonate (0.93 mmole, 3 equiv.). The mixture was stirred at 0° C. for 1 hour, then a solution of 80 mg of crude Part S aldehyde in 1 ml of DME was added to the reaction mixture. After stirring at 25° C. for 1 hour, the reaction was quenched with glacial acetic acid, then concentrated. The residue was diluted with 30 ml of ether, then washed with two 10 ml portions of saturated NaHCO₃ ml of H₂O. The organic layer was dried over anhydrous MgSO₄ and then concentrated.

Purification was done on a silica gel column, with 10% ethyl acetate in hexanes at eluting solvents, to give 50 mg of title enone as a yellow oil.

U.
[3α(Z),4α(1E,3S)]-7-[Tetrahydro-4-(3-hydroxy-1-octenyl)-3-thienyl]-5-heptenoic acid, methyl ester To a solution of 100 mg of Part T enone (0.28 mmole) in 2 ml of methanol at 25° C. was added 69 mg of cerium trichloride (0.28 mmole, 1 equiv.). After stirring at 25° C. for 15 minutes, the mixture was cooled to 0° C. and 10.6 mg of sodium borohydride (0.28 mmole, 4 equiv.) was added. After stirring at 0° C. for 20 minutes the reaction mixture was poured into 40 ml of saturated NH₄Cl solution. The aqueous layer was extracted with three 20 ml portions of ether. The combined ethereal extract was dried over anhydrous MgSO₄ and concentrated to give 90 mg of a crude mixture of alcohol isomers (fast moving isomer and slow moving isomer). 28 mg of the title FMI was isolated after a column chromatography using 2% ethyl acetate in CH₂Cl₂ as eluting solvents.

EXAMPLE 2

[3α(Z),4α(1E,3S)]-7-[Tetrahydro-4-(3-hydroxy-1ocetenyl)-3-thienyl]-5-heptenoic acid To a solution of 28 mg of Example 1 ester (0.08 mmole) in 3 ml of THF, saturated with argon, was added at 25° C., 800 μl 1N lithium hydroxide solution. After stirring at 25° C. for 7 hours, the reaction mixture was concentrated. The residue was diluted with 5 ml of H₂O, acidified to pH 3 with a saturated oxalic acid solution and extracted with three 10 ml portions of ether. The combined ethereal layer was washed with 10 ml of H₂O, dried over anhydrous MgSO₄ and concentrated to give 25 mg of title compound as an oil.

TLC: Silica gel; 7% MeOH/CH₂Cl₂; R_f= ~0.5 Anal Calcd for C₁₉H₃₂O₃S: C, b 67.01; H, 9.47; S, 9.41; Found: C, 66.87; H, 9.36; S, 9.36

EXAMPLE 3

[3α(Z),4α(1E,3S)]-7-[4-(3-Cyclohexyl-3-hydroxy-1-propenyl)tetrahydro-3-thienyl]-5-heptenoic acid, methyl ester

A.
[3α(Z),4α(1E)]-7-[Tetrahydro-4-(3-cyclohexyl-3-oxo-1-propenyl)-3-thienyl]-5-heptenoic acid, methyl ester To a slurry of 67.2 mg of prewashed sodium hydride (50% in mineral oil, 1.4 mmole, 2 equiv.) in 2 ml of dry dimethoxyethane (DME) at 0° C. was added 409 mg of 2-oxo-2-cyclohexylethyl dimethyl phosphonate (1.75 mmole, 2.5 equiv.). The mixture was stirred at 25° C. under an argon atmosphere for 1 hour, then cooled to 0° C. To this mixture at 0° C. was added a solution of ca. 0.7 mmole of [3α(Z),4α]-7-[tetrahydro-4-formyl-3-thienyl]-5-heptenoic acid, methyl ester (prepared as described in Example 1, Part S) in 1 ml of DME. After stirring at 25° C. for 1 hour, the reaction was quenched with glacial acetic acid, then concentrated. The residue was diluted with 15 ml of ether and washed with two 10 ml portions of saturated NaHCO₃ and 10 ml of H₂O. The ethereal layer was dried over anhydrous MgSO₄ and concentrated.

The residue was flash chromatographed on a silica gel column, with 10% ethyl acetate in hexanes as eluting solvents, to give 95 mg of title enone.

B.
[3α(Z),4α(1E,3S)]-7-[4-(3-Cyclohexyl-3-hydroxy-1-propenyl)tetrahydro-3-thienyl]-5-heptenoic acid, methyl ester (Fast Moving Isomer)

and

C.
[3α(Z),4α(1E,3R)]-7-[4-(3-Cyclohexyl-3-hydroxy-1-propenyl)tetrahydro-3-thienyl]-5-heptenoic acid, methyl ester (Slow Moving Isomer)

To a solution of 95 mg of title A enone (0.26 mmole) in 1 ml of dry methanol at 25° C. was added 61 mg of title A cerium trichloride (0.26 mmole, 1 equiv.). After stirring at 25° C. for 15 minutes, the mixture was cooled to 0° C. and 10 mg of sodium borohydride (0.26 mmole, 4 equiv.) was added. The reaction mixture was stirred at 0° for 15 minutes then poured into 20 ml of a saturated NH₄Cl solution. The aqueous solution was extracted with four 10 ml portions of ether. The combined ethereal extract was dried over anhydrous MgSO₄ and concentrated to give 90 mg of an oil.

Separation and purification was done on an HPLC semipreparative column, with 0.5% ethyl acetate in CH₂Cl₂ as eluting solvents, to give 32 mg of title B isomer (FMI) and 27 mg of title C isomer (SMI).

EXAMPLE 3A

[3α(Z),4α(1E,3S)]-7-[4-(3-Cyclohexyl-3-hydroxy-1-propenyl)tetrahydro-3-thienyl]-5-heptenoic acid To a solution of 32 mg of Example 3 Part B ester (0.08 mmole) in 3.2 ml of dry THF, saturated with argon, was added 800 μl of a 1N lithium hydroxide solution. After stirring at 25° for 20 hours, the reaction mixture was concentrated. The residue was diluted with 3 ml of H₂O, acidified to pH 3 with a saturated solution of oxalic acid and then extracted with three 5 ml portions of ether. The combined ethereal extract was washed with 5 ml of H$_2$O, then dried over anhydrous MgSO$_4$ and concentrated to give 30 mg of a crude oil.

This oil was purified on a CC-7 silica gel column, with a gradient of ether/pentane as eluting solvents, to give 23.3 mg of title acid as an oil.

TLC: silica gel; 7% MeOH/CH$_2$Cl; R$_f$~0.5

Anal Calcd for C$_{20}$H$_{32}$O$_3$S, 0.19 H$_2$O: C, 67.48; H, 9.17; S, 9.01; Found: C, 67.48; H, 8.95; S, 8.70;

EXAMPLE 4

[3α(Z),4α(1E,3R)]-7-[4-(3-Cyclohexyl-3-hydroxy-1-propenyl)tetrahydro-3-thienyl]-5-heptenoic acid To a solution of 27 mg of the Example 3 Part C slow moving isomer (0.07 mmole) in 2.8 ml of dry THF, saturated with argon, at 25° C. was added 700 μl 1N lithium hydroxide solution. After stirring at 25° C. for 20 hours, the mixture was concentrated. The residue was diluted with 3 ml of H$_2$O, acidified to pH 3 with a saturated solution of oxalic acid and extracted with three 10 ml portions of ether. The combined ethereal extract was washed with two ml portions of H$_2$O, dried over anhydrous MgSO$_4$ and concentrated to give 25 mg of a crude oil.

Purification was done on a CC-7 silica gel column, with a gradient of ether/pentanes as eluting solvents, to give 19.6 mg of title acid as an oil.

TLC: silica gel; 7% MeOH/CH$_2$Cl$_2$; R$_f$~0.5 Anal Calcd for C$_{20}$H$_{32}$O$_3$S; 0.19 H$_2$O: C, 67.48; H, 9.17; S, 9.01; Found: C, 67.48; H, 9.01; S, 8.86;

EXAMPLE 5

[3α(Z),4α(1E,3S)]-7-[Tetrahydro-4-(3-hydroxy-4,4-dimethyl-1-octenyl)-3-thienyl]-5-heptenoic acid, methyl ester

A.

[3α(Z),4α(1E)]-7-[Tetrahydro-4-(3-oxo-4,4-dimethyl-1-octenyl)-3-thienyl]-5-heptenoic acid, methyl ester To a slurry of 43.2 mg of sodium hydride (0.9 mmole, 2.2 eq., 50% dispersion in mineral oil) in 10 ml of dry DME at 0° C. under an argon atmosphere is added 316 mg of 2-oxo-3,3-dimethyl heptyl dimethyl phosphonate (1.2 mmole, 3.0 eq.). The mixture is stirred for 1 hour at 25° C., cooled to 0° C. and a solution of 100 mg of Example 1, Part S aldehyde, (0.41 mmole) in 5 ml of dry DME is added. After stirring at 25° C. for 30 minutes, the reaction is quenched with glacial acetic acid and concentrated. The residue is diluted with 50 ml of ether and washed with two 10 ml portions of saturated NaHCO$_3$ and 10 ml of H$_2$O. The organic layer is dried over anhydrous MgSO$_4$ and concentrated to give crude title enone which is used directly in the next reaction.

B.

[3α(Z),4α(1E,3S)]-7-[Tetrahydro-4-(3-hydroxy-4,4-dimethyl-1-octenyl)-3-thienyl]-5-heptenoic acid, methyl ester and

C.

[3α(Z),4α(1E,3R)]-7-[Tetrahydro-4-(3-hydroxy-4,4-dimethyl-1-octenyl)-3-thienyl]-5-heptenoic acid, methyl ester To crude Part A enone (ca. 0.41 mmole) in 2 ml of dry methanol at 25° C. is added 100 mg of cerium trichloride (0.41 mmole, 1 eq.). The mixture is stirred at 25° C. for 10 minutes, cooled to 0° C. and 15.6 mg of sodium borohydride (0.41 mmole, 4 eq.) is added. After stirring at 0° C. for 10 minutes, the reaction mixture is poured into 50 ml of a saturated NH$_4$Cl solution and extracted with three 20 ml portions of ether. The combined ethereal extract is dried over anhydrous MgSO$_4$ and concentrated.

Separation is done on silica gel column, eluting with 20% EtOAc/hexane to give 89 mg of title B ester and 23 mg of title C ester.

EXAMPLE 6

[3α(Z),4α(1E,3S)]-7-[Tetrahydro-4-(3-hydroxy-4,4dimethyl-1-octenyl)-3-furanyl]-5-heptenoic acid To a solution of Example 5, Part B methyl ester (0.24 mmole) in 10 ml of THF at 25° C. is added 2.4 ml of a 1N lithium hydroxide solution (2.4 mmole, 10 eq.). The mixture is stirred at 25° C. for 3 hours and then concentrated.

The residue is diluted with 5 ml of H$_2$O, acidified to pH 3 with a saturated oxalic acid solution and extracted with three 20 ml portions of ether. The combined ethereal extract is washed with two 10 ml portions of H$_2$O, dried over anhydrous MgSO$_4$ and concentrated to give 87 mg of an oil.

Purification is done on a CC-7 silica gel column, eluting with a gradient of pentane/ether. The product collected is kept under high vacuum for 3 days to yield 47 mg of title acid.

EXAMPLE 7

[3α(Z),4α(1E,3R)]-7-[Tetrahydro-4-(3-hydroxy-4,4dimethyl-1-octenyl)-3-thienyl]-5-heptenoic acid, methyl ester The title methyl ester was prepared as described in Example 5, Part C.

EXAMPLE 8

[3α(Z),4α(1E,3S,4S)]-7-[Tetrahydro-4-(3-hydroxy-4phenyl-1-pentenyl)-3-thienyl]-5-heptenoic acid, methyl ester

A.

[3α(Z),4α(1E,4S)]-7-[Tetrahydro-4-(3-oxo-4-phenyl-1-pentenyl)-3-thienyl]-5-heptenoic acid, methyl ester To a solution of 234.6 mg of (+)-2-oxo-4-methyl-4-phenylmethyl dimethyl phosphonate (0.9 mmole, 1.1 eq.) in 5 ml of dry THF at −78° C. under an argon atmosphere is added dropwise a solution of 371 μl of a 2.25M solution of n-butyl lithium in hexane (0.83 mm, 1.0 eq.). After stirring at −78° C. for 1 hour, the mixture was warmed to 25° C. and a solution of 200 mg of Example 1, Part S aldehyde (0.83 mmole) in 5 ml of dry THF is added. The reaction mixture is stirred at 25° C. for 1 hour then quenched with glacial acetic acid and concentrated. The residue is diluted with 50 ml of ether and washed with 20 ml of saturated NaHCO$_3$, 20 ml of H$_2$O, dried over anhydrous MgSO$_4$ and concentrated. Purification is done on a silica gel column, eluting with 20% EtOAc/hexane to give 230 mg of title enone.

B.

[3α(Z),4α(1E,3S,4S)]-7-[Tetrahydro-4-(3-hydroxy-4-phenyl-1-pentenyl)-3-thienyl]-5-heptenoic acid, methyl ester and

C.
[3α(Z),4α(1E,3R,4S)]-7-[Tetrahydro-4-(3-hydroxy-4-phenyl-1-pentenyl)-3-thienyl]-5-heptenoic acid, methyl ester To 230 mg of Part A enone (0.62 mmole) in 5 ml of methanol at 25° C. is added 151 mg of cerium trichloride (0.62 mmole, 1 eq.). After stirring at 25° C. for 10 minutes, the mixture is cooled to 0° C. and 23.6 mg of sodium borohydride is added (0.62 mmole, 4 eq.). The mixture is stirred at 0° C. for 10 minutes then poured into 50 ml of a saturated NH4Cl solution and extracted with three 30 ml portions of ether. The combined ethereal extract is washed with two 20 ml portions of H2O, dried over anhydrous MgSO4 and concentrated.

Separation is done on a silica gel column, eluting with 50% EtOAc/hexane to give 38 mg of title B ester ahd 100 mg of title C ester.

EXAMPLE 9
[3α(Z),4α(1E,3S,4S)]-7-[Tetrahydro-4-(3-hydroxy-4phenyl-1-pentenyl)-3-thienyl]-5-heptenoic acid To 38 mg of Example 8, Part B ester (0.1 mmole) in 4 ml of THF at 25° C. is added 1 ml of a 1M lithium hydroxide solution. The mixture is stirred at 25° C. for 20 hours and then concentrated. The residue is diluted with 5 ml of H2O, acidified to pH 3 with a saturated oxalic acid solution and extracted with three 10 ml portions of ether. The combined ethereal extract is washed with two 10 ml portions of H2O, dried over anhydrous MgSO4 and concentrated. The product is kept under high vacuum for 2 days to yield 22.5 mg of title acid as an oil.

EXAMPLE 10
[3α(Z),4β(1E,3S)]-7-[4-(3-Cyclohexyl-3-hydroxy-1-propenyl)tetrahydro-3-furanyl]-5-heptenoic acid, methyl ester

A.
[3α(Z),4β-7-[Tetrahydro-4-formyl-3-thienyl]-5-heptenoic acid, methyl ester To 140 mg of Example 1, Part S aldehyde (0.58 mmole) in 2 ml of methanol was added 3.15 mg of sodium methoxide (58 μmole, 10%). After stirring at 25° C. for 2 hours, the reaction mixture is poured into 50 ml of a saturated aqueous ammonium chloride solution and extracted with three 10 ml portions of ether. The organic layer is washed with 10 ml of H2O and dried over anhydrous MgSO4 and concentrated to give 130 mg of title aldehyde as an oil. This is used without purification.

B.
[3α(Z),4β(1E)]-7-[Tetrahydro-4-(3-oxo-3-cyclohexyl-1-propenyl)-3-thienyl]-5-heptenoic acid, methyl ester To a slurry of 28.6 mg of prewashed sodium hydride (50% dispersion in mineral oil, 0.6 mmole, 1.1 eq.) in 5 ml of dry dimethoxyethane (DME) at 0° C. is added 152 mg of 2-oxo-2-cyclohexylethyldimethylphosphonate (0.65 mmole, 1.2 eq.). After stirring at 25° C. for 1 hour, the mixture is cooled to 0° C. To this mixture is added a solution of 130 mg of title A aldehyde (0.54 mmole) in 5 ml of DME. The mixture is stirred at 25° C. for 30 minutes, then quenched with glacial acetic acid and concentrated. The residue is diluted with 30 ml of ether and washed with 10 ml of saturated NaHCO3, 10 ml of H2O, dried over anhydrous MgSO4 and concentrated to give 230 mg of crude title enone. This is used without purification.

C.
[3α(Z),4β(1E,3S)]-7-[4-(3-Cyclohexyl-3-hydroxy-1-propenyl)tetrahydro-3-thienyl]-5-heptenoic acid, methyl ester and

D.
[3α(Z),4β(1E,3R)]-7-[4-(3-Cyclohexyl-3-hydroxy-1-propenyl)tetrahydro-3-thienyl]-5-heptenoic acid, methyl ester To 230 mg of title B enone (ca. 0.56 mmole) in 3 ml of methanol at 25° C. is added 132 mg of cerium trichloride (0.56 mmole, 1 eq.). After stirring at 25° C. for 10 minutes, the mixture is cooled to 0° C. To this mixture is added 20.5 mg of sodium borohydride (0.56 mmole, 4 eq.). This is stirred at 0° C. for 10 minutes, then poured into 100 ml of a saturated NH4Cl solution, extracted with three 20 ml portions of ether, dried over anhydrous MgSO4 and concentrated. Separation is done on an LPS-1 silica gel column, eluting with 20% EtOAc/hexanes to give 105 mg of the desired title C allylic alcohol as an oil.

EXAMPLE 11
[3α(Z),4β(1E,3S)]-7-[4-(3-Cyclohexyl-3-hydroxy-1propenyl)tetrahydro-3-thienyl]-5-heptenoic acid To 95 mg of Example 10 methyl ester (0.27 mmole) in 8 ml of THF and 2 ml of H2O at 0° C. is added dropwise 2.7 ml of a 1M lithium hydroxide solution (2.7 mmole, 10 eq.). The mixture is stirred at 25° C. for three hours and then concentrated. The residue is diluted with 5 ml of H2O, acidified to pH 3 with a saturated oxalic acid solution and extracted with three 20 ml portions of ether. It is then dried over anhydrous MgSO4 and concentrated. The residue is purified on a CC-7 silica gel column, eluting with a gradient of pentane/ether.

The product is kept under high vacuum for 7 days to give 65 mg of title acid as a clear oil.

EXAMPLE 12
[3α(Z),4β(1E,3R)]-7-[4-(3-Cyclohexyl-3-hydroxy-1-propenyl)tetrahydro-3-thienyl]-5-heptenoic acid, methyl ester The title compound is prepared as described in Example 10, Part D.

EXAMPLE 13
[3α(Z),4β(1E,3R)]-7-[4-(3-Cyclohexyl-3-hydroxy-1-propenyl)tetrahydro-3-thienyl]-5-heptenoic acid To 54 mg of Example 12 ester (0.15 mmole) in 8 ml of THF and 2 ml of H2O at 0° C. is added dropwise 1.5 ml of a 1N lithium hydroxide solution (1.5 mmole, 10 eq.). The mixture is stirred at 25° C. for 4 hours and then concentrated. The residue is diluted with 5 ml of H2O, acidified to pH 3 with a saturated oxalic acid solution, extracted with three 20 ml portions of ether, dried over anhydrous MgSO4 and concentrated. The residue is purified on a CC-7 silica gel column, eluting with a gradient of pentane/ether. The product is kept under high vacuum for 2 days to give 50 mg of title acid as an oil.

EXAMPLE 14

[3α(Z),4β(1E,3S,4S)]-[Tetrahydro-4-(3-hydroxy-4-phenyl-1-pentenyl)-3-thienyl]-5-heptenoic acid, methyl ester

A.

[3α(Z),4β(1E)]-7-[Tetrahydro-4-(3-oxo-4-phenyl-1-pentenyl)-3-thienyl]-5-heptenoic acid, methyl ester To a solution of 166.6 mg of (+)-2-oxo-4-methyl-4-phenylmethyl dimethyl phosphonate (0.64 mmole, 1.1 eq.) in 5 ml of dry THF at −78° C. under an argon atmosphere is added dropwise a solution of 263.4 ml of a 2.5M solution of n-butyllithium in hexane (0.59 mm, 1.0 eq.). After stirring at −78° C. for 1 hour, the mixture is warmed to 25° C. and a solution of 140 mg of Example 10, Part A aldehyde (0.59 mmole) in 5 ml of dry THF is added. After stirring at 25° C. for 2 hours, the reaction is quenched with glacial acetic acid and concentrated. The residue is diluted with 50 ml of ether and washed with 20 ml of saturated $NaHCO_3$, 20 ml of $H_2O$, dried over anhydrous $MgSO_4$ and concentrated.

The residue is purified on a silica gel column, eluting with 20% EtOAc/hexanes to give 117 mg of title enone as an oil.

B.

[3α(Z),4β(1E,3S,4S)]-7-[Tetrahydro-4-(3-hydroxy-4-phenyl-1-pentenyl)-3-thienyl]-5-heptenoic acid, methyl ester and

C.

[3α(Z),4β(1E,3R,4S)]-7-[Tetrahydro-4-(3-hydroxy-4-phenyl-1-pentenyl)-3-thienyl]-5-heptenoic acid, methyl ester To 117 mg of title A enone (0.31 mmole) in 5 ml of methanol at 25° C. is added 77 mg of cerium trichloride (0.31 mmole, 1 eq.). After stirring at 25° C. for 10 minutes the mixture is cooled to 0° C., 12 mg of sodium borohydride (0.31 mmole, 4 eq.) is added and the mixture is stirred at 0° C. for 15 minutes. The reaction mixture is then poured into 50 ml of a saturated $NH_4Cl$ solution and extracted with three 20 ml portions of ether. The combined ethereal extract is dried over anhydrous $MgSO_4$ and concentrated to give 107 mg of a mixture.

Separation is done on a silica gel column, eluting with 25% EtOAc/hexane to give 50 mg of title C ester and 25 mg of title B ester.

EXAMPLE 15

[3α(Z),4β(1E,3S,4S)]-7-[Tetrahydro-4-(3-hydroxy-4phenyl-1-pentenyl)-3-thienyl]-5-heptenoic acid To 25 mg of Example 14 ester (0.07 mmole) in 2.8 ml of THF at 25° C. is added 0.7 ml of a 1M lithium hydroxide solution (0.7 mmole, 10 eq.). The mixture is stirred at 25° C. for 20 hours, and then concentrated. The residue is diluted with 5 ml of $H_2O$, acidified to pH 3 with a saturated oxalic acid solution and extracted with three 10 ml portions of ether. The combined ethereal extract is washed with two 10 ml portions of $H_2O$, dried over anhydrous $MgSO_4$ and concentrated. The product is kept under high vacuum for 2 days to yield 20 mg of title acid as an oil.

EXAMPLE 16

[3α(Z),4β(1E,3R,4S)]-7-[Tetrahydro-4-(3-hydroxy-4-phenyl-1-pentenyl)-3-thienyl]-5-heptenoic acid To 60 mg of Example 14 Part C methyl ester (0.16 mmole) in 4 ml of THF and 1 ml of $H_2O$ at 0° C. is added dropwise 1.6 ml of a 1M lithium hydroxide solution (1.6 mmole, 10 eq.). The mixture is stirred at 25° C. for 6 hours and then concentrated. The residue is diluted with 5 ml of $H_2O$ and acidified to pH 3 with a saturated oxalic acid solution, extracted with three 20 ml portions of ether, dried over anhydrous $MgSO_4$ and concentrated. The residue is purified on a CC-7 silica gel column, eluting with a gradient of pentane/ether.

The product is kept under high vacuum for 2 days to give 26 mg of title acid as an oil.

EXAMPLE 17

[3α(Z),4α(1E,3S)]-7-[Tetrahydro-4-(3-hydroxy-1-octenyl)-3-thienyl]-2,5-heptadienoic acid

A.

[3α(Z),4α(1E,3S)]-7-[Tetrahydro-4-(3-tetrahydropyranoxy-1-octenyl)-3-thienyl]-5-heptenoic acid, methyl ester To a solution of 2.37 g of [3α(Z),4α(1E,3S)]-7-[tetrahydro-4-(3-hydroxy-1-octenyl)-3-thienyl]-5-heptenoic acid, methyl ester (prepared as described in Example 1) (7.0 mmole) in 20 ml of dry methylene chloride is added with stirring a catalytic amount of p-toluene sulfonic acid, followed by 720 μl of dihydropyran (DHP) (8.0 mmole) at 0°–5° C. The reaction mixture is stirred at 0°–5° C. for 40 minutes, whereupon it is washed with aqueous sodium bicarbonate solution. The methylene chloride layer is separated and the aqueous layer is extracted with ether. The combined organic extract is dried over anhydrous magnesium sulfate and concentrated under reduced pressure. Purification by flash chromatography on a silica gel column gives 2.75 g of desired title THP-ether (eluting solvent 10–15% ethylacetate in hexane).

B.

[3α(Z),4α(1E,3S)]-7-[Tetrahydro-4-(3-tetrahydropyranoxy-1-octenyl)-3-thienyl]-2-selenophenyl-5-heptenoic acid, methyl ester To a solution of 2 ml of distilled diisopropylamine (13 mmole, distilled over $CaH_2$) in 30 ml of dry THF, cooled at −78° C. in a dry ice-acetone bath is added dropwise 7.5 ml of a 1.6M solution of n-butyllithium in hexane (12 mmole). The solution of lithium diisopropylamide so formed is stirred at −78° C. for 30 minutes, whereupon a solution of 2.53 g of Part A THP-ether (6 mmole) in 15 ml of dry THF is added dropwise over a period of 10 minutes. The colorless solution is stirred at −78° C. for an additional 30 minutes, whereupon a solution of 3.75 g of diphenyl-diselenide (12 mmole) in 5 ml of dry THF is added dropwise. Initially the yellow color of diselenide discharges immediately upon addition. The yellow solution is stirred at −78° C. for 30 minutes, whereupon the cooling bath is removed. After 30 minutes, the reaction mixture is quenched by addition of aqueous ammonium chloride solution. It is then diluted with water and the organic layer is separated. The aqueous layer is extracted with ether. The combined organic extract is dried over anhydrous magnesium-sulfate and concentrated under reduced pressure. The crude residue is chromatographed on a silica gel column. Elution with 5–15% ethyl acetate in hexane gives 2.89 g of title α-selenophenyl ester as a colorless oil.

C.
[3α(Z),4α(1E,3S)]-7-[Tetrahydro-4-(3-tetrahydropyranoxy-1-octenyl)-3-thienyl]-2-selenophenyl-5-heptenoic acid To a solution of 1.36 g of Part B seleno-ester (~2 mmole) in 12 ml of distilled THF and 3 ml of water is added with stirring 9 ml of a 1N aqueous lithium hydroxide solution. The heterogeneous reaction mixture is stirred at room temperature under an argon atmosphere for 2 days, whereupon it is acidified by careful addition of 2N aqueous hydrochloric acid solution. Extraction with ether (X3), drying of the ether extract over anhydrous magnesium sulfate and finally concentration under reduced pressure gives 1.3 g of desired title acid as a colorless oil.

D.
[3α(Z),4α(1E,3S)]-7-[Tetrahydro-4-(3-tetrahydropyranoxy-1-octenyl)-3-thienyl]-2,5-heptadienoic acid A solution of 423 mg of Part C α-selenophenyl acid (0.73 mmole) in 10 ml of distilled THF is treated with 500 μl of a 30% aqueous hydrogen peroxide solution at 0°–5° C. After a few minutes, the cooling bath is removed and the reaction mixture is stirred at room temperature for 1 hour. It is then diluted with ether and washed several times with water. The organic extract is dried over anhydrous magnesium sulfate and concentrated under reduced pressure. The crude oil is chromatographed on a CC-7 silica gel column and eluted with 20–50% ethyl acetate in hexane to obtain 245 mg of title acid.

E.
[3α(Z),4α(1E,3S)]-7-[Tetrahydro-4-(3-hydroxy-1-octenyl)-3-thienyl-2,5-heptadienoic acid A solution of 245 mg of Part D α,β-unsaturated acid in 10 ml of dimethoxy ethane and 3 ml of 2N HCl is stirred at room temperature for 8 hours. The reaction mixture is diluted with ether and washed thoroughly with water. The aqueous layer is re-extracted with ether twice. The combined organic extract is dried over anhydrous magnesium sulfate and concentrated under reduced pressure. The crude residue is chromatographed on a CC-7 silica gel column and eluted with 20–50% ethyl acetate in hexane to obtain 185 mg of title 2,3-dehydro acid.

EXAMPLE 18
[3α(Z),4α(1E,3S)]-7-[Tetrahydro-4-(3-hydroxyoctenyl)-3-thienyl]heptanoic acid

A.
3α,4α)-7-[Tetrahydro-4-(1-hydroxy-1-hydroxymethylmethyl)-3-thienyl]-heptanoic acid, methyl ester A mixture of 500 mg of Example 1 Part R diol, 100 mg of a 10% palladium over carbon in 80 ml of EtOAc and 4 ml of glacial acetic acid is shaken in a Parr bottle under 50 lb. of hydrogen pressure at 25° C. for 24 hours. The mixture is then filtered through a bed of Celite. The filtrate is concentrated to give title A diol.

B. (3α,4α)-7-[Tetrahydro-4-formyl-3-thienyl]heptanoic acid, methyl ester

To a solution of 272 mg of title A diol (1 mmole) in 5 ml methanol at 25° C. is added a solution of 230 mg of sodium m-periodate in 1 ml H$_2$O. The mixture is stirred at 25° C. for 30 minutes, then extracted with 3–10 ml portions of CH$_2$Cl$_2$. The organic layer is dried over anhydrous MgSO$_4$ and concentrated to give title aldehyde.

C.
[3α,4α(1E,3S)]-7-[Tetrahydro-4-(3-hydroxy-1-octenyl)-3-thienyl]-heptanoic acid Following the procedure of Example 1 Parts T and U and Example 2 except substituting the above Part B aldehyde for the Example 1 Part S aldehyde, the title acid is obtained.

EXAMPLE 19
[3α(Z),4α(1E,3S)]-7-[Tetrahydro-4-(3-hydroxy-3phenyl-1-propenyl)-3-thienyl]-5-heptenoic acid Following the procedure of Examples 1 and 2 phosphonate for 2-oxo-heptyldimethylphosphonate, the title compound is obtained.

EXAMPLE 20
[3α(Z),4α(1E,3S)]-7-[Tetrahydro-4-(3-hydroxy-4-phenyl-1-butenyl)-3-thienyl]-5-heptenoic acid Following the procedure of Examples 1 and 2 except substituting 2-oxo-3-phenyl propyldimethylphosphonate for 2-oxo-heptyldimethylphosphonate, the title compound is obtained.

EXAMPLE 21
[3α(Z),4α(1E,3S)]-7-[Tetrahydro-4-(3-hydroxy-4cyclohexyl-1-butenyl)-3-thienyl-5-heptenoic acid Following the procedure of Examples 1 and 2 except substituting 2-oxo-3-cyclohexyl propyldimethylphosphonate for 2-oxo-heptyldimethylphosphonate, the title compound is obtained.

EXAMPLE 22
[3α(Z),4α(1E,3S)]-7-[Tetrahydro-4-(3-hydroxy-2ethoxy-1-propenyl)-3-thienyl]-5-heptenoic acid Following the procedure of Examples 1 and 2 except substituting 2-oxo-2-ethoxy ethyldimethylphosphonate for 2-oxo-heptyldimethylphosphonate, the title compound is obtained.

EXAMPLE 23
[3α(Z),4α(1E,3S)]-7-[4-(3-Cyclohexyl-3-hydroxy-1propenyl)tetrahydro-3-thienyl]-2,5-heptadienoic acid Following the procedure of Example 20 except substituting the Example 5 compound for the Example 1 compound in Part A, the title compound is obtained.

EXAMPLE 24
[3α(Z),4α(1E,3S)]-7-[Tetrahydro-4-(3-hydroxy-4-phenyl-1-pentenyl)-3-thienyl]-2,5-heptadienoic acid Following the procedure of Example 17 except substituting the Example 8 compound for the Example 1 compound in Part A, the title compound is obtained.

EXAMPLE 25

[3α(Z),4α(1E,3S)]-7-[Tetrahydro-4-(3-hydroxy-2ethoxy-1-propenyl)-3-thienyl]-5-heptenoic acid Following the procedure of Examples 1 and 2 except substituting the Example 22 compound for the Example 1 compound in Part A, the title compound is obtained.

EXAMPLE 26

[3α(Z),4α(1E,3S)]-7-[Tetrahydro-4-(3-hydroxy-4,4dimethyl-1-octenyl)-3-thienyl]heptanoic acid Following the procedure of Example 18 and Examples 5 and 6 except substituting the Example 18 Part B aldehyde for the Example 1, part S aldehyde used in Example 5 Part A, the title compound is obtained.

EXAMPLE 27

[3α(Z),4α(1E,3S)4]-7-[Tetrahydro-4-(3-hydroxy-4phenyl-1-pentenyl)-3-thienyl]heptanoic acid Following the procedure of Example 18 and Examples 8 and 9 except substituting the Example 18 Part B aldehyde for the Example 1 Part S aldehyde used in Example 8 Part A, the title compound is obtained.

EXAMPLE 28

[3α(Z),4β(1E,3S)]-7-[4-(3-Cyclohexyl-3-hydroxy-1-propenyl)tetrahydro-3-thienyl]heptanoic acid Following the procedure of Example 18 and Examples 10 and 11 except substituting the Example 18 Part B aldehyde for the Example 1 Part S aldehyde used in Example 10 Part A, the title compound is obtained.

EXAMPLE 29

[3α(Z),4α(1E,3S)]-7-[Tetrahydro-4-(3-hydroxy-1octyl)-3-thienyl]-5-heptenoic acid, methyl ester

A.

[3α(Z),4α(1E,3S)]-7-[Tetrahydro-4-(3-oxo-1-octyl)-3-thienyl]-5-heptenoic acid, methyl ester To a suspension of 686 mg of purified cuprous bromide (4.8 mmole) in 12 ml of dry THF, cooled at 0°-5° C. is added with stirring 1.35 ml of a 3.5M solution of red-Al (sodium bis(2-methoxyethoxy)aluminum hydride) in toluene dropwise. The solution is stirred at 0°-5° C. for 30 minutes, whereupon it is cooled to −78° C. and 2 ml of n-butanol (18 mmole) is added rapidly, followed by a solution of 672 mg of Example 1 Part T enone (2 mmole) in 4 ml of dry THF. After 10 minutes at −78° C., the reaction mixture is warmed to −20° C. and left for an additional 1 hour. The reaction mixture is quenched by addition of 70 ml of water and then poured into saturated ammonium chloride solution and extracted with ether (X3). The ether extract is dried over anhydrous magnesium sulfate, filtered and the filtrate is concentrated under reduced pressure. 675 Mg of desired title ketone is obtained.

B.

[3α(Z),4α(1E,3S)]-7-[Tetrahydro-4-(3-hydroxy-1-octyl)-3-thienyl]-5-heptenoic acid, methyl ester To a solution of 338 mg of Part A ketone (1 mmole) in 2 ml of methanol and 2 ml of dry THF is added with stirring 400 mg of ceric (III) chloride hydrate (1 mmole). After stirring at room temperature for 10 minutes, the reaction mixture is cooled to −50° C. and 38 mg of solid sodium borohydride (~1 mmole) is added to the reaction mixture. The reaction mixture is stirred at −50° C. for 45 minutes, whereupon 5 ml of acetone is added to destroy excess of borohydride. The mixture is stirred for an additional 5 minutes at −50° C. The cooling bath is removed and the reaction mixture is evaporated to dryness. The crude residue is diluted with ether and washed with 1N aqueous hydrochloric acid solution. The ether extract is dried over anhydrous MgSO4 and concentrated under reduced pressure. The crude residue is chromatographed on a silica gel column and eluted with 30-50% ethyl acetate in hexane to obtain the desired 3S-alcohol.

EXAMPLE 30

[3α(Z),4α(1E,3S)]-7-[Tetrahydro-4-(3-hydroxy-1-octyl)-3-thienyl]-5-heptenoic acid Following the procedure of Example 2 except substituting the Example 29 methyl ester for the Example 1 methyl ester, the title compound is obtained.

EXAMPLE 32

[3α(Z),4α(1E,3S)]-7-[Tetrahydro-4-(3-hydroxy-4,4dimethyl-1-octenyl)-3-thienyl]-5-heptenoic acid, methyl ester and free acid Following the procedure of Examples 29 and 30 except substituting the Example 5 Part A ketone for the Example 1 Part T ketone, the title compound is obtained.

EXAMPLE 33

[3α(Z),4α(1E,3S,4S)]-7-[Tetrahydro-4-(3-hydroxy-4phenyl-1-pentyl)-3-thienyl]-5-heptenoic acid, methyl ester and free acid Following the procedure of Examples 29 and 30 except substituting the Example 8 Part A ketone for the Example 1 Part T ketone, the title compound is obtained.

EXAMPLE 34

[3α(Z),4β(1E,3S)]-7-[4-(3-Cyclohexyl-3-hydroxy-1propyl)tetrahydro-3-thienyl]-5-heptenoic acid, methyl ester and free acid Following the procedure of Examples 29 and 30 except substituting the Example 10 Part A ketone for the Example 1 Part T ketone, the title compound is obtained.

EXAMPLE 35 to 44

It will be appreciated that following the procedure as described in the specification and in the working Examples as outlined above, any of the following compounds may be prepared

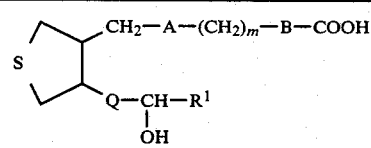

| Ex. No. | A | m | B | Q | R¹ |
|---|---|---|---|---|---|
| 35 | CH=CH | 4 | — | CH=CH | C4H9 |
| 36 | CH=CH | 5 | CH=CH | CH=CH | C6H5 |

-continued

| Ex. No. | A | m | B | Q | R¹ |
|---------|---|---|---|---|-----|
| 37 | CH—CH₂ CH₃ | 6 | CH=CH | (CH₂)₂ | cyclohexyl |
| 38 | — | 7 | CH=CH | (CH₂)₂ | C₆H₅CH₂ |
| 39 | (CH₂)₂ | 6 | — | (CH₂)₂ | C₅H₁₁ |
| 40 | (CH₂)₂ | 8 | — | CH=CH | C₃H₇O |
| 41 | (CH₂)₂ | 3 | — | (CH₂)₂ | C₆H₅(CH₂)₂ |
| 42 | CH=CH | 2 | — | CH=CH | C₂H₅O |
| 43 | CH=CH | 1 | CH=CH | (CH₂)₂ | cyclopentyl-CH₂ |
| 44 | CH=CH | 3 | — | CH=CH | CH₃O |

EXAMPLE 45

[3α(Z),4α(1E,3S)]-7-[4-(3-hydroxy-1-propyl)tetrahydro)-3-thienyl]-2,5-heptadienoic acid Following the procedure of Example 17 except substituting the Example 31 methyl ester for the Example 1 methyl ester, the title compound is obtained.

EXAMPLE 46

[3α(Z),4α(1E,3S)]-7-[Tetrahydro-4-(3-hydroxy-1-octyl)-3-thienyl]-2,5-heptadienoic acid Following the procedure of Example 17 except substituting the Example 29 methyl ester for the Example 1 methyl ester, the title compound is obtained.

EXAMPLE 47

[3α(Z),4α(1E,3S)]-7-[Tetrahydro-4-(3-hydroxy-4,4-dimethyl-1-octyl)-3-thienyl]-2,5-heptadienoic acid Following the procedure of Example 17 except substituting the Example 32 methyl ester for the Example 1 methyl ester, the title compound is obtained.

EXAMPLE 48

[3α(Z),4α(1E,3S)]-7-[Tetrahydro-4-(3-hydroxy-4-phenyl-1-pentyl)-3-thienyl]-2,5-heptadienoic acid Following the procedure of Example 17 except substituting the Example 33 methyl ester for the Example 1 methyl ester, the title compound is obtained.

EXAMPLE 49

[3α(Z),4α(1E,3S)]-7-[4-(3-Cyclohexyl-3-hydroxy-1-propyl)-3-thienyl]-2,5-heptadienoic acid Following the procedure of Example 17 except substituting the Example 34 methyl ester for the Example 1 methyl ester, the title compound is obtained.

What is claimed is:
1. A compound of the structure

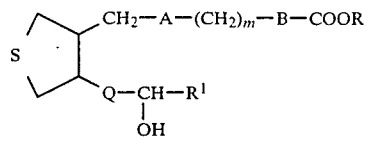

including all stereoisomers thereof, wherein A is $(CH_2)_n$, —CH=CH— or a single bond; m is 1 to 8; B is —CH=CH— single bond, but where B is —CH=CH—, m is 1 to 6; Q is —CH=CH— or —(CH₂)$_n$—; n is 1 to 4; R is H, lower alkyl or alkali metal; and R¹ is lower alkyl, aryl, arylalkyl, cycloalkyl, cycloalkylalkyl or lower alkoxy.

2. The compound as defined in claim 1 wherein said compound is the cis isomer.

3. The compound as defined in claim 1 wherein said compound is the trans isomer.

4. The compound as defined in claim 1 wherein A is —CH=CH—.

5. The compound as defined in claim 1 wherein R is H.

6. The compound as defined in claim 1 wherein m is 2 to 5 and B is a single bond.

7. The compound as defined in claim 1 wherein Q is —CH=CH—.

8. The compound as defined in claim 1 wherein R¹ is butyl, pentyl, hexyl or heptyl phenyl or cycloalkyl, including all isomers thereof.

9. The compound as defined in claim 1 having the name [3α(Z),4α(1E,3S)]-7-[tetrahydro-4-(3-hydroxy-1-octenyl)-3-thienyl]-5-heptenoic acid or the methyl ester thereof, including all stereoisomers thereof.

10. The compound as defined in claim 1 having the name [3α(Z),4α(1E,3R)]-[tetrahydro-4-(3-hydroxy-1-octenyl)-3-thienyl]-5-heptenoic acid or the methyl ester thereof, including all stereoisomers thereof.

11. The compound as defined in claim 1 having the name [3α(Z),4α(1E,3S)]-7-[4-(3-cyclohexyl-3-hydroxy-1-propenyl)tetrahydro-3-thienyl]-5-heptenoic acid or the methyl ester thereof, including all stereoisomers thereof.

12. The compound as defined in claim 1 having the name [3α(Z),4α(1E,3R)]-7-[4-(3-cyclohexyl-3-hydroxy-1-propenyl)tetrahydro-3-thienyl]-5-heptenoic acid or the methyl ester thereof, including all stereoisomers thereof.

13. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

14. The method as defined in claim 13 wherein said compound is administered in an amount within the range of from about 1 to about 100 mg/kg.

15. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

16. A method of inhibiting platelet aggregation which comprises administering to a mammalian host an effective amount of a compound as defined in claim 1 or a pharmaceutically acceptable salt thereof.

17. A method of inhibiting bronchoconstriction associated with asthma, which comprises administering to a mammalian host an effective amount of a compound as defined in claim 1 or a pharmaceutically acceptable salt thereof.

18. A method for treating peripheral vascular disease, which comprises topically or systemically administering to a mammalian host an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,638,011
DATED : January 20, 1987
INVENTOR(S) : Jagabandhu Das

It is certified that error appears in the above-identified patent and that said Letters Patent is hereby corrected as shown below:

Column 32, line 10, before "single bond" insert --or a--.

Signed and Sealed this

Seventeenth Day of November, 1987

Attest:

DONALD J. QUIGG

Attesting Officer

Commissioner of Patents and Trademarks